(12) United States Patent
Kukreja et al.

(10) Patent No.: US 11,816,633 B2
(45) Date of Patent: *Nov. 14, 2023

(54) ORDER STATUS

(71) Applicant: CVS Pharmacy, Inc., Woonsocket, RI (US)

(72) Inventors: Vijay I. Kukreja, Cumberland, RI (US); Domenic Vecchiarelli, North Attleboro, MA (US); Himanshu Gupta, Johnston, RI (US); Dianna Southiseng, Woonsocket, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/955,144

(22) Filed: Sep. 28, 2022

(65) Prior Publication Data

US 2023/0019964 A1    Jan. 19, 2023

Related U.S. Application Data

(63) Continuation of application No. 17/061,175, filed on Oct. 1, 2020, now Pat. No. 11,488,105, which is a continuation of application No. 14/829,191, filed on Aug. 18, 2015, now abandoned.

(51) Int. Cl.
| | |
|---|---|
| G06Q 10/087 | (2023.01) |
| G16H 10/60 | (2018.01) |
| G16H 20/10 | (2018.01) |
| G16H 70/40 | (2018.01) |
| G06F 16/25 | (2019.01) |
| G06Q 10/10 | (2023.01) |
| G06Q 50/22 | (2018.01) |

(52) U.S. Cl.
CPC ......... *G06Q 10/087* (2013.01); *G06F 16/258* (2019.01); *G06Q 10/10* (2013.01); *G06Q 50/22* (2013.01); *G16H 10/60* (2018.01); *G16H 20/10* (2018.01); *G16H 70/40* (2018.01)

(58) Field of Classification Search
None
See application file for complete search history.

(56) References Cited

U.S. PATENT DOCUMENTS

| | | |
|---|---|---|
| 7,870,007 B1 | 1/2011 | Francis et al. |
| 8,311,853 B1 | 11/2012 | Pankow et al. |
| 9,485,237 B1 | 11/2016 | Johansson et al. |
| 10,210,311 B1 | 2/2019 | Taneja |
| 10,235,499 B1 | 3/2019 | Bleser et al. |
| 2002/0052760 A1 | 5/2002 | Munoz et al. |
| 2009/0077129 A1 | 3/2009 | Blose |
| 2011/0166878 A1 | 7/2011 | Louie et al. |

(Continued)

OTHER PUBLICATIONS

Anonymous, "CVS Pharmacy on the App Store on iTunes," retrieved from https://web.archive.org/web/20150318165700/https://itunes.apples.com/us/app/cvs-pharmacy/id395545555?mt=8 on Oct. 4, 2016, 2 pgs.

(Continued)

*Primary Examiner* — Devin C Hein
(74) *Attorney, Agent, or Firm* — PATENT LAW WORKS LLP

(57) ABSTRACT

Given information identifying a user who is not logged into a system, the user is provided a guest order status of one or more pharmacy orders; the guest order status masks sensitive information of the user.

20 Claims, 10 Drawing Sheets

(56) References Cited

U.S. PATENT DOCUMENTS

| 2014/0180707 | A1 | 6/2014 | Kukreja et al. |
| 2014/0282949 | A1 | 9/2014 | Nath et al. |
| 2014/0379371 | A1 | 12/2014 | Tran et al. |
| 2016/0357937 | A1 | 12/2016 | Walter et al. |

OTHER PUBLICATIONS

Anonymous, "Walgreens—Refill Prescriptions," retrieved from www.walgreens.com/pharmacy on Oct. 4, 2016, 1 pg.

Barlas, "Mediare Changes Include New Part D Rules and Possible Cuts to Hospitals," Prescription: Washington, 2013, v. 38, No. 6, p. 312.

International Search Report and Written Opinion for International Application No. PCT/US2016/047332, dated Oct. 21, 2016, 16 pgs.

300

Order Status

Requested: May 15, 2015
Member's DOB: January 23, 1955
Shipping to: 123 Main Street, Anytown, USA
Status: Shipped on May 29, 2015

Rx #: *****1234
Order #: *****6789
Name: Li*****
Dose: 5 mg
Quantity: 90 / 90 days' supply
Doctor: Dr. Sm***
Cost: $32.00

320

Order Status

| | |
|---|---|
| Requested: | May 15, 2015 |
| Member's DOB: | January 23, 1955 |
| Shipping to: | 123 Main Street, Anytown, USA |
| Status: | Shipped on May 29, 2015 |

| | |
|---|---|
| Rx #: | ████1234 |
| Order #: | ████6789 |
| Name: | Li████ |
| Dose: | 5 mg |
| Quantity: | 90 / 90 days' supply |
| Doctor: | Dr. Sm████ |
| Cost: | $32.00 |

FIG. 3B

340 

Order Status

Requested: May 15, 2015
Member's DOB: January 23, 1955
Shipping to: 123 Main Street, Anytown, USA
Status: Awaiting consent Rx #: *****1234
Order #: *****6789
Name: Li*****
Dose: 5 mg
Quantity: 90 / 90 days' supply
Doctor: Dr. Sm***
Cost: $32.00

Consent (action required)

According to Medicare rules, we need your consent to ship medications you didn't order directly from us, which may include prescriptions sent to us by a doctor or enrolled in our auto-refill program.
Ship this medication?
O Yes          O Not now          342

Order Status

Requested: May 15, 2015
Member's DOB: ▓▓▓▓▓▓▓▓
Shipping to: ▓▓▓▓▓▓▓▓▓▓▓▓▓▓▓▓
Status: Shipped on May 29, 2015

Rx #: ▓▓▓▓▓▓
Order #: ▓▓▓▓▓▓
Name: ▓▓▓▓▓▓
Dose: ▓▓▓▓▓▓
Quantity: ▓▓▓▓▓▓
Doctor: ▓▓▓▓▓▓
Cost: ▓▓▓▓▓▓

FIG. 3D

ORDER STATUS

CROSS-REFERENCE TO RELATED APPLICATIONS

The present application is a continuation of U.S. patent application Ser. No. 17/061,175, titled "Order Status," and filed on Oct. 1, 2020, which is a continuation of U.S. patent application Ser. No. 14/829,191, titled "Order Status," and filed on Aug. 18, 2015, the content of which are hereby incorporated by reference in their entireties.

TECHNICAL FIELD

Embodiments of the present invention relate generally to pharmaceutical sales and, more particularly, to providing status information regarding the order status of pharmaceutical sales.

BACKGROUND

Customers of pharmacies may be prescribed medication by their doctors or from other sources and may each have any number of different prescriptions. These prescriptions may be newly prescribed or may be refills of previously prescribed medication; the refills may be automatic or may require a doctor's approval before further refills are prescribed. Managing each prescription may be difficult or time-consuming for a patient, and a patient may miss one or more days or weeks of treatment if a prescription expires before the patient can fill or refill it if the status of the filling or refilling is not known.

Existing systems and methods may allow a patient to view his or her prescription status by means of a user account accessible to the patient via a client device, such as a computer, tablet, or smartphone. The patient may log into his or her account using a username and password, and the host server may access the patient's account and cause the display of information such as prescription status on the screen of the client device. This system may be inconvenient for the patient, however, because it requires input of the username and password, and the patient may not have access to, remember, or have time to retrieve that access information. Further, some patients may not have a user account previously configured; for these patients, accessing their prescription status requires the additional step of account creation. A need therefor exists for a more convenient and simpler way for patients to access their prescription status information.

SUMMARY

Embodiments of the present invention include systems and methods for providing a limited or "guest" prescription order status to patients. In various embodiments, a patient enters identifying information into a client device and transmits that information to a server; the server retrieves prescription status information given the patient information, masks sensitive information from the status information, and transmits the masked status information back to the client for display thereon. In various embodiments, the patients enters his or her date of birth and a prescription ("Rx") number, but any identifying information is within the scope of the present invention.

In one aspect, a system for providing guest order statuses for pharmacy orders includes a non-volatile computer memory for storing status information for a plurality of pharmacy orders made by a plurality of users; a network interface configured for transmitting and receiving data over a computer network; and a computer processor for executing software instructions. The instructions include receiving, from a client device via the network interface, information identifying a user; retrieving, from the computer memory, using the received identifying information, a status of an order placed by the user; masking sensitive information in the status; and transmitting the masked information to the client device for presentation to the user.

In various embodiments, the user is not logged into the system. The information identifying the user may include a date of birth of the user and a prescription number, a Social-Security number, a telephone number, an email address, a street address, an order number, and/or a benefit member number. The sensitive information may include a prescription number, an order number, a medication name, and/or a prescribing doctor name. The user may be prompted for consent for shipping the order. The client device may be a desktop computer, laptop computer, tablet computer, smartphone, or telephone. The user may be prompted for additional information if the received information identifying the user is insufficient to identify the user. The amount of information masked may depend on the amount or quality of information identifying the user.

In another aspect, a method for providing guest order statuses for pharmacy orders includes receiving, from a client device via a network interface, information identifying a user; retrieving, from the computer memory, using the received identifying information, a status of an order placed by the user; masking, using a computer processor, sensitive information in the status; and transmitting the masked information to the client device via the network interface for presentation to the user.

In various embodiments, the user is not logged into the system. The information identifying the user may include a date of birth of the user and a prescription number, a Social-Security number, a telephone number, an email address, a street address, an order number, and/or a benefit member number. The sensitive information may include a prescription number, an order number, a medication name, and/or a prescribing doctor name. The user may be prompted for consent for shipping the order. The client device may be a desktop computer, laptop computer, tablet computer, smartphone, or telephone. The user may be prompted for additional information if the received information identifying the user is insufficient to identify the user. The amount of information masked may depend on the amount or quality of information identifying the user.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which:

FIGS. 3A-3D illustrate exemplary guest order status output interfaces in accordance with embodiments of the present invention;

DETAILED DESCRIPTION

Various embodiments of the present invention include systems and methods for providing a guest order status of an ordered medication to a patient of a pharmacy. A patient may access a server via a client device; the patient inputs identifying information into the client device and transmits it to the server. The patient need not be logged into an account on the server or even have an account configured. The server retrieves the status of one or more orders associated with the patient and masks sensitive information in the status before transmitting the masked status back to the client for display thereon. The identifying information may be, for example, the date of birth and prescription number of the patient. The unmasked information may include the date of the request, the patient's date of birth, the shipping address, the shipping status, the quantity of the medication, and the price of the order. The masked, sensitive information may include the patient's name, prescription number, order number, and the name of the medication.

Figure 1:
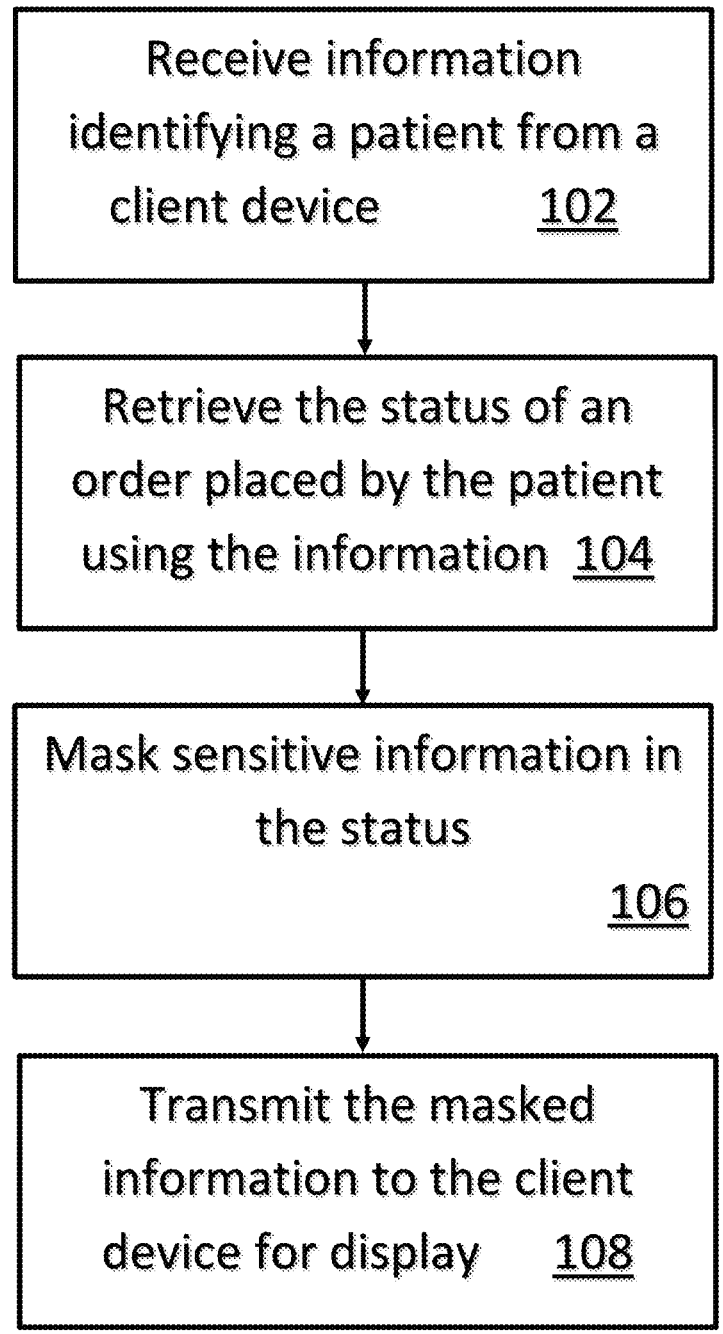
FIG. 1 illustrates a method for providing a guest order status in accordance with an embodiment of the present invention.

FIG. 1 illustrates a method 100 for providing a guest order status in accordance with embodiments of the present invention. A server receives (102), from a client device, information identifying a patient user. The client device may be a desktop computer, laptop computer, tablet computer, smartphone, or any other similar electronic device, and the patient may enter the identification information using a keyboard, mouse, touchscreen, voice input, or any other similar input device. The information may be transmitted from the client to the server over any suitable computer network, such as the Internet, by any means known in the art (such as, for example, TCP/IP). The user may click or select a user-interface element, such as a button, to transmit the information, or the information may be transmitted automatically as the user enters it.

The information input by the user may be used to uniquely identify the user, some or all of the prescription orders placed by the user, or both. In one embodiment, the information includes the user's date of birth and a prescription number. The present invention is not limited, however, to any particular type or amount of information. In other embodiments, the information includes the user's first, middle, and/or last name, address, email address, telephone number, Social Security number, benefit member number, order number, zip code, store number, or any other similar information.

Once the information is received, the server retrieves (104) the status of one or more orders placed by the user therewith. The server may include, for example, a database or similar data-storage system that contains order status information for any number of users; this database may be searchable using any number of keys, such as date of birth or prescription number. The server may query the database using the information received from the user and receive, in response, the status of some or all orders placed by the user.

The server may then mask (106) sensitive information in the status. In some embodiments, the server masks a predetermined number and type of fields in the status, such as the user's name, the name of the medication, the name of the user's doctor or prescribing physician, or other similar information. In other embodiments, the user has a user account on the server (though he or she may not be logged into it at the time of the status request) and may specify which fields and information he or she wants shown or masked. In another embodiment, the server determines how much information to mask based on a degree of confidence that (a) the user has been correctly identified and (b) the status request is being made by the user and not a third-party impostor.

Once the information is masked, the server transmits (108) the masked information back to the client for display thereon. The masking may be performed such that the information beneath the masking is never transmitted to the client, thus preventing a malicious client or other third party from uncovering the masked information by (for example) examining any metadata transmitted with the masked information. The masked information may be displayed on any screen or touchscreen, and the user may be given the option to save it or print it.

Figure 2A:
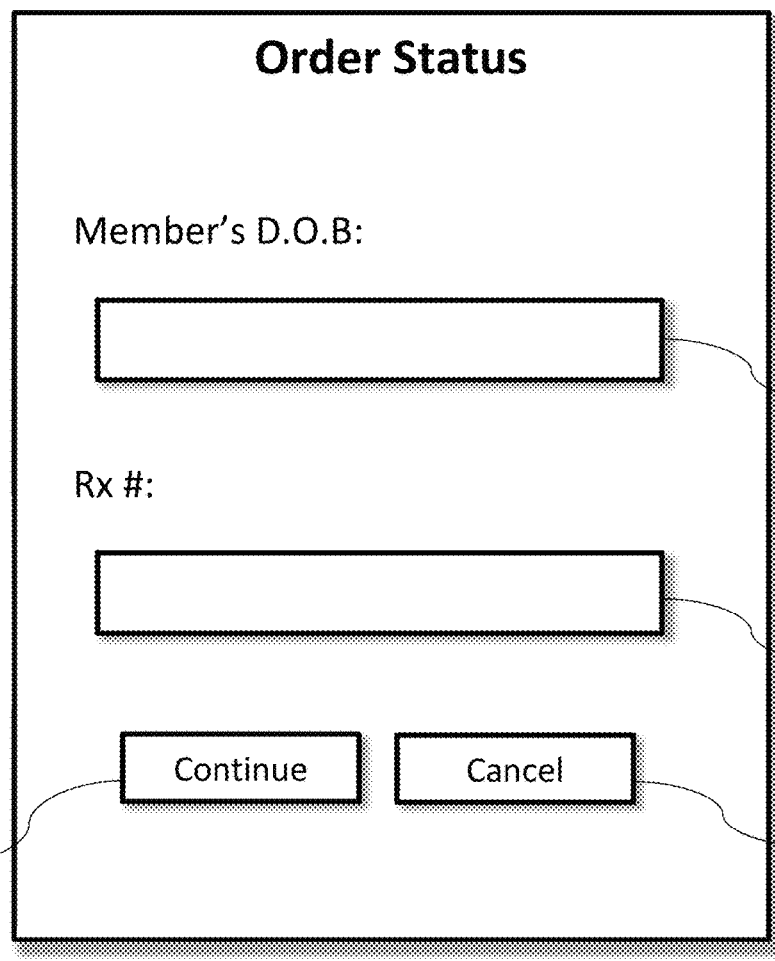
FIGS. 2A-2C illustrate exemplary patient-information input interfaces in accordance with embodiments of the present invention.

FIG. 2A illustrates an example of a user input interface 200 for display on a client device. A first entry box 202 is configured to receive a user's date of birth, and a second entry box 204 is configured to receive a prescription number. The entry boxes 202, 204 may be configured to accept information in different formats (e.g., DD/MM/YY or DD-MM-YYYY for the date of birth) or may present the user with format templates, selection menus, or similar user-interface elements to aid the user in inputting the information. A warning may appear if the information is entered incorrectly or if, for example, the user enters a prescription number that doesn't exist or is too short or too long. Once the user has inputted the information, he or she may select a "continue" interface element 206 to transmit the information to the server. The user may alternatively select a "cancel" interface element 208 to cancel the status request.

Figure 2B:
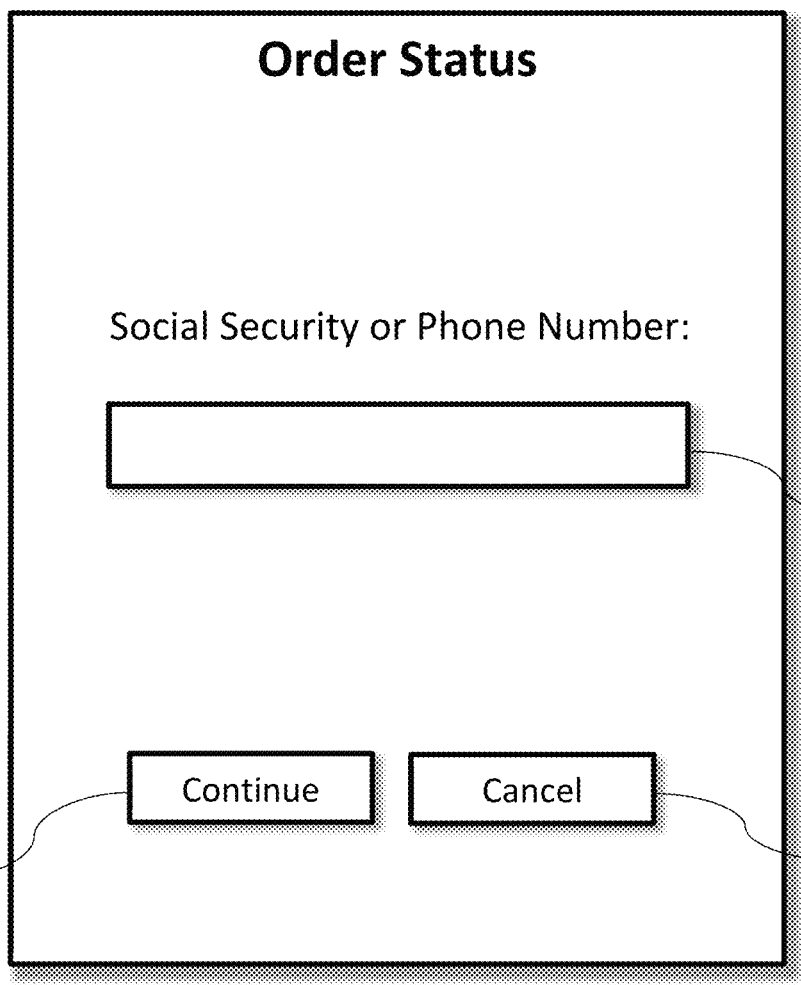

FIG. 2B illustrates another example of a user input interface 220. In this example, only one item of information is requested from a single entry box 222—the Social-Security number or phone number of the user. Other possibilities for the single item of information include prescription number, order number, email address, or any other item of information that may uniquely identify the user to the server. In various embodiments, as explained in greater detail below, the server may mask additional information when only one item of identifying information is provided because, for example, there may be a greater risk that the user is not uniquely identified and/or the requestor is not the user. As in the previous example, the user may select user interface elements to continue 224 or cancel 226.

Figure 2C:
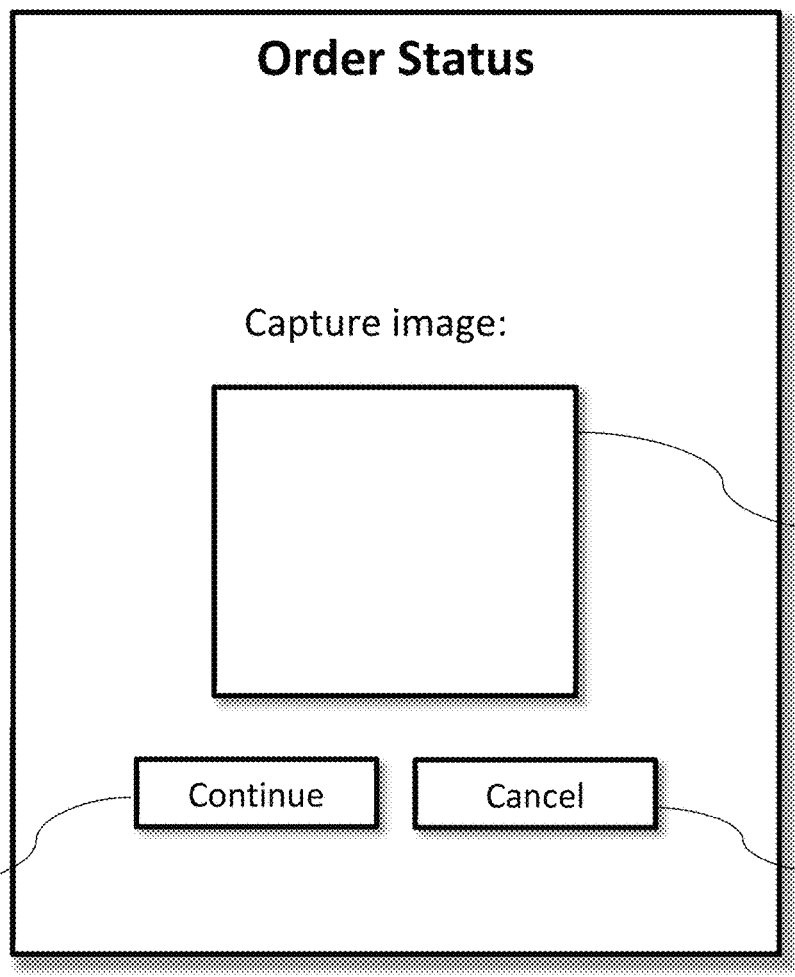

FIG. 2C illustrates another example of a user input interface 240. In this example, the user is presented with an image-capture interface 242 for capturing an image using, for example, a camera or scanner attached to or integrated into the client device. The user may use the interface 240 to capture an image of an object or objects that provide information identifying the user, such as the label of a prescription bottle already in the user's possession or a driver's license or other ID card belonging to the user. In one embodiment, the user has previously uploaded an image to the server using, for example, the user's account on the server, and the new picture captured by the user is compared against the previously uploaded image to identify the user. In one embodiment, the image includes the face or fingerprint of the user. Any other method of identifying the user via a previously uploaded item of information is within the scope of the present invention; in various embodiments, the previously uploaded information includes a pattern, signature, or challenge-and-answer questions.

In some embodiments, the server is unable to uniquely identify the user given the provided information. In these cases, the server may prompt the user for additional information by transmitting another request for information to the client or may simply transmit an error message stating that the user's status is unavailable due to insufficient information provided.

In other embodiments, the client device is a telephone, and the user interface provided to the user is an audio interface. Given audio cues, the user may speak or input via a telephone number pad the requested information, such as date of birth and prescription number. The server may then provide the information described above as unmasked (such as order status) via audio.

Figure 3A:

FIG. 3A illustrates an order status 300 that includes masked information in accordance with embodiments of the present invention. In this embodiment, a request date, date of birth, shipping address, order status, dose amount, quantity, and price appear unmasked, while a prescription number, order number, medication name, and doctor name appear masked. Any selection of masked and unmasked information is within the scope of the present invention, however. The information is masked using asterisks; any method of masking is within the scope of the present invention, however, such as the black boxes shown in the order status 320 of FIG. 3B.

In some embodiments, as shown in the order status 340 of FIG. 3C, a consent dialog 342 is displayed to the user. Some prescriptions may require the explicit consent of the user before they may be shipped if, for example, the order for the prescription originated from a third party. The consent dialog 342 present the user with an input dialog to give this consent, such as by selecting a "Yes" radio button.

FIG. 3D illustrates an order status 360 in which additional information is masked (as compared to the order status 300 of FIG. 3A. In this embodiment, the order status shows only the request date and shipping status; all other information is masked. The order status 360 may be transmitted to the client and displayed thereon if the identity of the user is uncertain, such as when the user provides only one item of identifying information (with reference to FIG. 2B) or when a facial or signature match of the user is unreliable.

Figure 4:
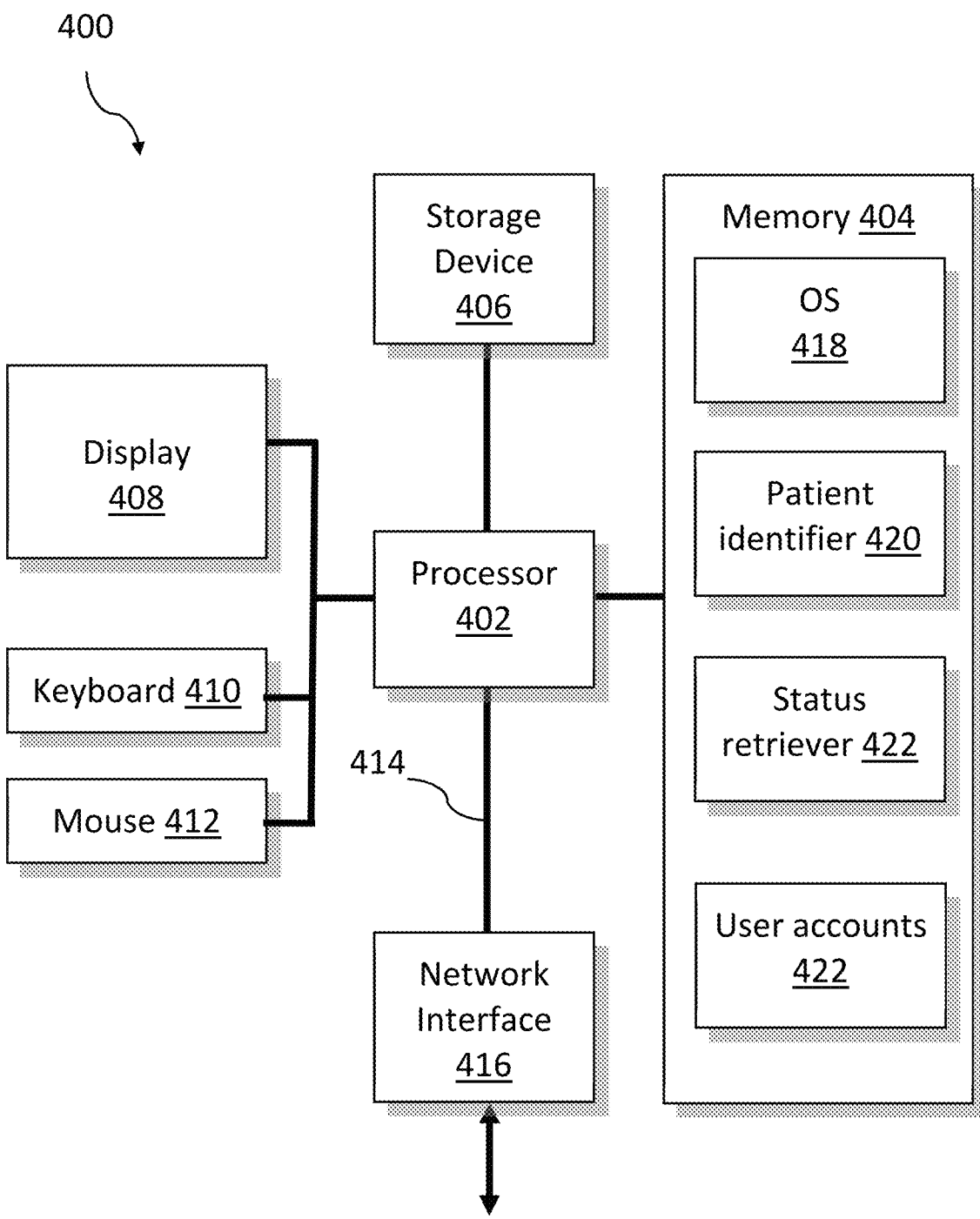
FIG. 4 illustrates a server system for providing a guest order status in accordance with an embodiment of the present invention.

FIG. 4 is a simplified block diagram of a suitably programmed general-purpose server 400 implementing embodiments of the present invention. The server 400 includes a processor 402 having one or more central processing units (CPUs), volatile and/or non-volatile main memory 204 (e.g., RAM, ROM, or flash memory), one or more mass storage devices 206 (e.g., hard disks, or removable media such as CDs, DVDs, USB flash drives, etc. and associated media drivers), a display device 408 (e.g., a liquid-crystal display (LCD) monitor), user-input devices such as a keyboard 410 and a mouse 412, and one or more buses 414 (e.g., a single system bus shared between all components, or separate memory and peripheral buses) that facilitate communication between these components. A network interface 416 (e.g., a Wi-Fi or ETHERNET port) may be used to connect the computer 400 to the Internet or other network.

The main memory 404 may be used to store instructions to be executed by the processor 402, conceptually illustrated as a group of modules. These modules generally include an operating system 418 (e.g., a Microsoft WINDOWS, Linux, or APPLE OS X operating system) that directs the execution of low-level, basic system functions (such as memory allocation, file management, and the operation of mass storage devices), as well as higher-level software applications, such as a user identifier 420 and an order status retriever 422. The various modules may be programmed in any suitable programming language, including, without limitation high-level languages such as C, C++, Java, Perl, Python, or Ruby or low-level assembly languages. The memory 404 may further store input and/or output data associated with execution of the instructions (including, e.g., user-account data 224) as well as additional information used by the various software applications.

Figure 5:
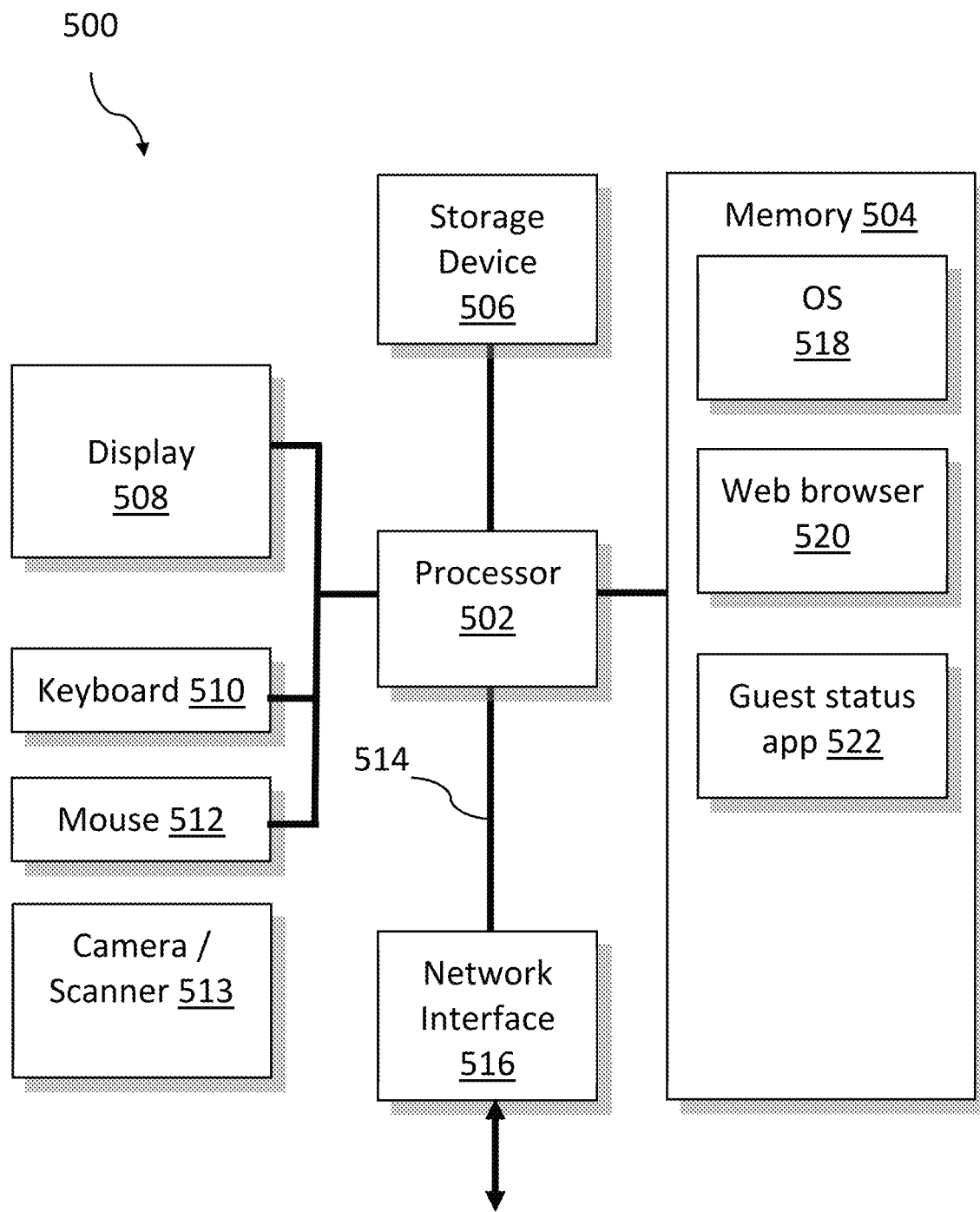
FIG. 5 illustrates a client system for receiving patient information and displaying a guest order status in accordance with an embodiment of the present invention.

FIG. 5 is a simplified block diagram of a suitably programmed client device 500 for capturing information from a user and displaying an order status thereto. Like the server 400, the client device 500 includes a processor 502, a memory 504, a storage device 506, a display 508, a keyboard 410, a mouse 412, buses 414, and a network interface 416. The client 500 may further include a camera/scanner 413 for capturing images. The client 500 and the server 400 may communicate via a network such as the Internet using the network interfaces 416, 516. The user input and output interfaces described herein may be presented to the user via a web browser 520 and/or a client-native application 522.

The server 400 and client 500 are described herein with reference to particular blocks, but this description is not intended to limit the invention to a particular physical arrangement of distinct component parts. The computer 400 is an illustrative example; variations and modifications are possible. Computers may be implemented in a variety of form factors, including server systems, desktop systems, laptop systems, tablets, smartphones or personal digital assistants, and so on. A particular implementation may include other functionality not described herein, e.g., wired and/or wireless network interfaces, media playing and/or recording capability, etc. In some embodiments, one or more cameras may be built into the computer rather than being supplied as separate components. Further, the computer processor may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method comprising:
   receiving an input from a user, wherein:
      the input comprises user identifier information and a first medication prescription number; and
      the first medication prescription number is associated with a first prescribed medication;
   validating that the user has been correctly identified by the input;
   retrieving a plurality of orders associated with a user identified based on the first medication prescription number, wherein:
      the plurality of orders include a first order and a second order;
      the first order is associated with a first prescribed medication prescribed to the user and the first medication prescription number;
      the second order is associated with a second prescribed medication prescribed to the user and a second medication prescription number; and
      the first medication prescription number and the second medication prescription number are different;
   determining a level of less than all of the information related to the plurality of orders to mask based on validating that the user has been correctly identified;
   masking at least a portion of sensitive information related to the first order and at least a portion of sensitive information related to the second;
   generating a first prescribed medication processing status related to the first prescribed medication;
   generating a second prescribed medication processing status related the second prescribed medication; and
   transmitting a first order status and a second order status, wherein:
      the first order status comprises a first unmasked portion of the sensitive information related to the first order, and the first prescribed medication processing status related to the first prescribed medication; and
      the second order status comprises a second unmasked portion of the sensitive information related to the second order and the second prescribed medication processing status related to the second prescribed medication.

2. The method of claim 1, further comprising:
   determining whether the first order originated from a third party; and
   prompting the user to consent to ship the first order in response to determining that the first order originated from the third party.

3. The method of claim 1, wherein the user is not logged into a system, the method comprising:
   providing, via a client device, the first order status and the second order status.

4. The method of claim 1, further comprising:
   determining information identifying the user, the information comprising a date of birth of the user and a prescription number.

5. The method of claim 1, further comprising:
   determining information identifying the user, wherein the information comprises one of a telephone number, a street address, an order number, or a benefit member number.

6. The method of claim 1, wherein the sensitive information further comprises an order number, and a prescribing doctor name.

7. The method of claim 1, further comprising:
   generating a degree of confidence that the user has been correctly identified by the input; and
   determining a level of information to mask based on the degree of confidence that a status request is being made by the user and not a third-party imposter.

8. The method of claim 7, further comprising:
   prompting the user for additional information if the input for identifying the user is insufficient to identify the user.

9. The method of claim 1, wherein the sensitive information that is masked depends on an amount or quality of information identifying the user.

10. A system comprising:
    a non-volatile computer memory for storing instructions;
    a computer processor for executing the instructions, thereby causing the system to:
       receive an input from a user, wherein:
          the input comprises user identifier information and a first medication prescription number; and
          the first medication prescription number is associated with a first prescribed medication;
       validate that the user has been correctly identified by the input;
       retrieve a plurality of orders associated with a user identified based on the first medication prescription number, wherein:
          the plurality of orders include a first order and a second order;
          the first order is associated with a first prescribed medication prescribed to the user and the first medication prescription number;
          the second order is associated with a second prescribed medication prescribed to the user and a second medication prescription number; and
          the first medication prescription number and the second medication prescription number are different;
       determine a level of less than all of the information related to the plurality of orders to mask based on validating that the user has been correctly identified;
       mask at least a portion of sensitive information related to the first order and at least a portion of sensitive information related to the second;
       generate a first prescribed medication processing status related to the first prescribed medication;
       generate a second prescribed medication processing status related the second prescribed medication; and transmit a first order status and a second order status, wherein:

the first order status comprises a first unmasked portion of the sensitive information related to the first order, and the first prescribed medication processing status related to the first prescribed medication; and the second order status comprises a second unmasked portion of the sensitive information related to the second order and the second prescribed medication processing status related to the second prescribed medication.

11. The system of claim 10, wherein the computer processor is further configured for executing software instructions to:

determine whether the first order originated from a third party; and prompt the user to consent to ship the first order in response to determining that the first order originated from the third party.

12. The system of claim 10, wherein the user is not logged into the system, the system comprising a client device for providing the first order status and second order status.

13. The system of claim 10, wherein the computer processor is further configured for executing software instructions to:

determine information to identify the user, wherein the information comprises a date of birth of the user and a prescription number.

14. The system of claim 10, wherein the computer processor is further configured for executing software instructions to:

determine information to identify the user, wherein the information comprises one of a telephone number, a street address, an order number, or a benefit member number.

15. The system of claim 10, wherein the sensitive information further comprises an order number, and a prescribing doctor name.

16. The system of claim 10, wherein the computer processor is further configured for executing software instructions to:

generate a degree of confidence that the user has been correctly identified by the input; and determine a level of information to mask based on the degree of confidence that a status request is being made by the user and not a third-party imposter.

17. The system of claim 16, wherein the computer processor is further configured for executing software instructions to:

prompt the user for additional information if the input for identifying the user is insufficient to identify the user.

18. The system of claim 10, wherein the sensitive information that is masked depends on an amount or quality of information identifying the user.

19. A non-transitory computer readable medium, the non-transitory computer-readable medium containing program instructions that cause one or more computers to perform a method comprising:

receiving an input from a user, wherein:

the input comprises user identifier information and a first medication prescription number; and the first medication prescription number is associated with a first prescribed medication;

validating that the user has been correctly identified by the input;

retrieving a plurality of orders associated with a user identified based on the first medication prescription number, wherein:

the plurality of orders include a first order and a second order;

the first order is associated with a first prescribed medication prescribed to the user and the first medication prescription number;

the second order is associated with a second prescribed medication prescribed to the user and a second medication prescription number; and the first medication prescription number and the second medication prescription number are different;

determining a level of less than all of the information related to the plurality of orders to mask based on validating that the user has been correctly identified;

masking at least a portion of sensitive information related to the first order and at least a portion of sensitive information related to the second;

generating a first prescribed medication processing status related to the first prescribed medication;

generating a second prescribed medication processing status related the second prescribed medication; and transmitting a first order status and a second order status, wherein:

the first order status comprises a first unmasked portion of the sensitive information related to the first order, and the first prescribed medication processing status related to the first prescribed medication; and the second order status comprises a second unmasked portion of the sensitive information related to the second order and the second prescribed medication processing status related to the second prescribed medication.

20. The non-transitory computer-readable medium of claim 19, further storing program instructions that cause the one or more computers to perform the method further comprising:

generating a degree of confidence that the user has been correctly identified by the input; and determining a level of information to mask based on the degree of confidence that a status request is being made by the user and not a third-party imposter.

* * * * *